(12) United States Patent
Caramenico, III et al.

(10) Patent No.: US 10,398,656 B1
(45) Date of Patent: Sep. 3, 2019

(54) COMPOSITIONS AND METHODS FOR THE TREATMENT OF VIRAL SKIN DISEASE

(71) Applicant: Veloce BioPharma, LLC, Ft. Lauderdale, FL (US)

(72) Inventors: Nicholas J. Caramenico, III, Norristown, PA (US); Joseph Capriotti, Christiansted, VI (US); Kara Capriotti, Fort Washington, PA (US)

(73) Assignee: Veloce BioPharma, LLC, Fort Lauderdale, FL (US)

( * ) Notice: Subject to any disclaimer, the term of this patent is extended or adjusted under 35 U.S.C. 154(b) by 0 days.

(21) Appl. No.: 15/985,596

(22) Filed: May 21, 2018

(51) Int. Cl.
*A61K 31/10* (2006.01)
*A61P 17/12* (2006.01)
*A61K 9/00* (2006.01)
*A61K 47/38* (2006.01)

(52) U.S. Cl.
CPC ............ *A61K 31/10* (2013.01); *A61K 9/0014* (2013.01); *A61K 47/38* (2013.01); *A61P 17/12* (2018.01)

(58) Field of Classification Search
CPC ...... A61K 31/10; A61K 47/38; A61K 9/0014; A61P 17/12
See application file for complete search history.

(56) References Cited

U.S. PATENT DOCUMENTS

| | | | | |
|---|---|---|---|---|
| 3,740,420 A | * | 6/1973 | Herschler et al. ... | A61K 9/0014 424/45 |
| 2004/0096410 A1 | * | 5/2004 | Maley ................... | A61K 31/00 424/70.1 |
| 2013/0295291 A1 | * | 11/2013 | Crowley .............. | C09D 183/02 427/387 |
| 2017/0000819 A1 | * | 1/2017 | Capriotti ................ | A61K 31/79 |

OTHER PUBLICATIONS

Rubin (Part II. Toxicology, Fate, and Metabolism, Toxicity of Dimethyl Sulfoxide, Alone and in Combination, pp. 98-103, published 1975) (Year: 1975).*
WebMD pp. 1-4 (Year: 2016).*

* cited by examiner

*Primary Examiner* — Yevgeny Valenrod
*Assistant Examiner* — Blaine G Doletski
(74) *Attorney, Agent, or Firm* — Studebaker & Brackett PC

(57) ABSTRACT

A composition comprising dimethyl sulfoxide (DMSO) as an effective agent useful for treating skin diseases or conditions caused by, associated with, or are complicated by microbial infection is disclosed.

14 Claims, No Drawings

COMPOSITIONS AND METHODS FOR THE TREATMENT OF VIRAL SKIN DISEASE

BACKGROUND

Skin diseases and conditions, such as acne, dermatitis, rosacea, common warts, molluscum contagiosum, onychomycosis, and paronychia can be the result of a primary viral, bacterial or fungal infection and also can be further complicated by way of secondary or opportunistic microbial colonization and/or bacterial, fungal or viral infection. Despite the attempts made by the medical and pharmaceutical industry to develop treatments and drugs for these diseases and conditions, the causative agents have remained difficult to treat and the resulting diseases and conditions difficult to cure.

Acne

Acne is a well-known and common skin disease that can present in different forms as well as grades of severity, ranging from simple acne vulgaris to the more dangerous forms, such as acne conglobate, which can lead to severe disfigurements of the skin. Disregarding these conditions by forgoing treatment, or even improper or excessive treatment, can lead to irreversible scars and changes of the skin, and consequent adverse effects to quality of life.

Molluscum Contagiosum

Molluscum contagiosum (MC) is a viral infection of the skin. It is caused by a DNA poxvirus called the MC virus. The virus that causes MC spreads from direct contact person-to-person by touching the affected lesion. The disease may also be transmitted via fomites. The skin infection is most common in children and sexually active adults. MC can affect any area of the skin but is most common on the trunk of the body, arms, groin, and legs. MC is contagious until the lesions are resolved. Most lesions will resolve without treatment but can persist for years, if not treated. The average length of infection is between 6-18 months. Though there are many anecdotal remedies, none of them were shown to be effective in prospective clinical trials.

Onychomycosis

Onychomycosis—nail fungal infection—affects 30-60 million patients each year in the United States. It is the most common disease of the nails and constitutes about a half of all nail abnormalities. This condition may affect toenails or fingernails, but toenail infections are particularly common. The prevalence of onychomycosis is about 6-8% of the United States adult population. Common signs of onychomycosis include a thickened, yellow, or cloudy appearance of the nails. The nails can become rough and crumbly and can separate from the nail bed. Patients with onychomycosis may experience significant psychosocial problems due to the appearance of the nail.

The causative pathogens of onychomycosis include dermatophytes, *Candida*, and non-dermatophytic molds. Dermatophytes are the fungi most commonly responsible for onychomycosis in the temperate western countries, while *Candida* and non-dermatophytic molds are more frequently involved in the tropics and subtropics with a hot and humid climate. *Trichophyton rubrum* is a common dermatophyte involved in onychomycosis. Other dermatophytes that may be involved are *T. mentagrophytes, Epidermophyton floccosum, T. violaceum, Microsporum gypseum, T. tonsurans, T. soudanense* and the cattle ringworm fungus *T. verrucosum*.

*Candida* spp. are known to cause fingernail onychomycosis in people whose hands are often submerged in water. Nondermatophytic molds, in particular members of the mold genera *Scytalidium* (now called *Neoscytalidium*), *Scopulariopsis*, and *Aspergillus* mainly affect people in the tropics, though it can persist if they later move to areas of temperate climate. Control of these pathogens can be used to treat onychomycosis.

Paronychia

Paronychia is one of the most common infections of the hand and nails. The entire nail plate is surrounded by the perionychium, which consists of proximal and lateral nail folds, and the hyponychium, the area beneath the free edge of the nail. Paronychias are localized, superficial infections or abscesses of the perionychium (epidermis bordering the nails). Paronychial infections develop when a disruption occurs between the seal of the proximal nail fold (commonly called the cuticle) and the nail plate that allows a portal of entry for invading organisms or irritants. Clinically, the disease referred to as paronychia is divided into acute paronychia (duration less than six weeks) or chronic paronychia (duration of the condition more than six weeks.) Paronychia associated with certain disease states and medication, particularly anti-cancer chemotherapeutics, can be extremely recalcitrant to treatment.

Acute Paronychia

Acute paronychia most commonly results from nail biting, finger sucking, aggressive manicuring, a hang nail or penetrating trauma, with or without a retained foreign body. The most common infecting organism is *Staphylococcus aureus*, followed by *streptococci* and *pseudomonas* organisms. Gram-negative organisms, herpes simplex virus, dermatophytes and yeasts have also been reported as causative agents. Children are prone to acute paronychia through direct inoculation of fingers with flora from the mouth secondary to finger sucking and nail biting. Patients with acute paronychia may report localized pain and tenderness of the perionychium. The perionychial area usually appears erythematous and inflamed, and the nail may appear discolored and even distorted. If left untreated, a collection of pus may develop as an abscess around the perionychium. Fluctuance and local purulence at the nail margin may occur, and infection may extend beneath the nail margin to involve the nail bed. Conservative treatment, such as warm-water soaks three to four times a day, may be effective early in the course if an abscess has not formed. Clindamycin (Cleocin) and the combination of amoxicillin-clavulanic acid (Augmentin) are effective against most pathogens isolated from these infections. When abscess or fluctuance is present, efforts to induce spontaneous drainage or surgical drainage become necessary.

Chronic Paronychia

Chronic paronychia resembles acute paronychia clinically, but the cause is multi-factorial. Chronic paronychia is usually non-suppurative and is more difficult to treat. For irritant-induced chronic paronychia, people at risk include those who are repeatedly exposed to water containing irritants or alkali, and those who are repeatedly exposed to moist environments. Persons at high risk include bartenders, housekeepers, homemakers, dishwashers and swimmers, as well as diabetic and immunosuppressed persons. Diseases associated with paronychia include autoimmune bullous disorders, psoriasis, and lichen planus. Paronychia is a well-known side effect of numerous targeted anticancer therapies, with Epidermal Growth Factor Inhibitors being the most widely reported causative class. Chronic paronychia usually causes swollen, red, tender and boggy nail folds. Symptoms are typically present for six weeks or longer. Fluctuance is rare, and there is less erythema than is present in acute paronychia. *Candida albicans* may be cultured from 95 percent of cases of chronic paronychia.

Other pathogens, including atypical mycobacteria, gram-negative rods and gram-negative cocci, have also been implicated in chronic paronychia. Treatment of chronic paronychia primarily involves avoiding predisposing factors such as exposure to irritating substances, prolonged exposure to water, manicures, nail trauma and finger sucking. Treatment with a combination of topical steroids and an antifungal agent has been shown to be successful. Oral antifungal therapy is rarely necessary. Treatment of potential secondary bacterial infections with antibacterial solutions or ointments, acetic acid soaks (1:1 ratio of vinegar to water) or oral antibiotics may be necessary. Surgical intervention is indicated when medical treatment fails. Excellent results have been reported with the use of an eponychial marsupialization technique, as well as removal of the entire nail and application of an antifungal-steroid ointment to the nail bed.

Paronychia is Increasing with Newer Cancer Therapies

Overexpression of the epidermal growth factor receptor (EGFR) is strongly associated with cancer development and progression of a number of malignancies. EGFR inhibitors (EGFRI) are targeted agents used for treating lung (erlotinib), pancreatic (erlotinib in combination with gemcitabine), breast (lapatinib in combination with capecitabine or anastrozole), head and neck (cetuximab in combination with radiotherapy), and colorectal cancers (cetuximab, panitumumab)[i]. EGFRI may be used as first-line through third-line treatments, alone or in combination with other agents in the aforementioned cancers. Commonly experienced dermatologic side effects include papulopustular (acneiform) rash, hair changes, radiation dermatitis enhancement, pruritus, mucositis, xerosis/fissures, and paronychia. Incidences of these side effects are frequent. When severe, dermatologic toxicities may to lead to dose modification or discontinuation. Although the side effect profile may be primarily dermatologic, toxicities result in significant physical and emotional discomfort, thus it is critical to maximize supportive measures. EGFRI therapies are being used with increasing frequency for cancer because they are specifically targeted molecular therapies for individual cancer subsets that avoid the use of more toxic broad-sweeping chemotherapies. Because numerous structures in the epidermis (or superior most layer of the skin) share similar receptors, they have well-known side effects that result. Many patients on EGFRI therapy develop paronychia, which results in increased financial burden on the health care system. All patients receiving EGFRIs are at risk for developing nail changes, which typically develop after two or more months of chemotherapy exposure. Resultant onycholysis or onychodystrophy may result as a secondary process from the presence of nail matrix inflammation. Fingernails and toenails may be affected, with the first digits most commonly affected. Precedent trauma is not believed to be causative but rather an aggravating factor. Morbidity is high, leading to significant pain, functional limitation, and impairment of activities of daily living. There are no approved treatments for EGFRI-associated nail changes. Similarly, there have been no randomized controlled studies until our study described below evaluating therapies for paronychia. Management strategies are aimed at minimizing periungual trauma, decreasing periungual inflammation, preventing superinfection, and eliminating excessive granulation tissue. EGFRI are not the only class of medications to induce paronychia, as many other cancer chemotherapies and immunotherapies can cause chemotherapy-induced paronychia.

Dimethyl Sulfoxide (DMSO)

Dimethyl sulfoxide (DMSO) is a polar aprotic solvent that dissolves both polar and nonpolar compounds and is miscible in a wide range of organic solvents as well as water. It has a relatively high melting point.

DMSO has been used in medicine since the 1960's following the discovery that it could penetrate the skin without damage and could carry small molecules into a biological system. DMSO is predominantly used as a topical analgesic, a vehicle for topical application of pharmaceuticals, as an anti-inflammatory, and an antioxidant.

DMSO has been examined for the treatment of numerous conditions and ailments, but the U.S. Food and Drug Administration (FDA) has approved its use only for the symptomatic relief of patients with interstitial cystitis. A gel containing DMSO and two additional active ingredients, namely, dexpanthenol and heparin, is sold in Germany and eastern Europe for topical use in sprains, tendinitis, and local inflammation. DMSO is also marketed as an alternative medicine.

DMSO solution is commonly used in veterinary medicine as a liniment for horses, alone or in combination with other ingredients to carry those other ingredients across the skin. DMSO is used intravenously, alone or in combination with other drugs for the treatment of increased intracranial pressure and/or cerebral edema in horses.

According to WebMD (https://www.webmd.com/vitamins/ai/ingredientmono-874/dmso-dimethylsulfoxide) DMSO is available as a prescription medicine and dietary supplement and is most commonly used for bladder inflammation (interstitial cystitis).

DMSO is possibly effective for a chronic pain condition called complex regional pain syndrome, skin and tissue damage caused by chemotherapy when it leaks from the IV, and in combination with another active ingredient, e.g., idoxuridine, to reduce lesions and swelling and pain associated with shingles.

Research has shown that DMSO is likely ineffective for scleroderma or for treatment of cancer, but may have some effect for treating amyloidosis, bile duct stones, diabetic foot ulcers, high blood pressure in the brain, arthritis, stomach ulcers caused by *Helicobacter pylori*, tendinopathy, asthma, eye problems, gall stones, headaches, muscle problems, and calluses.

These prior uses of DMSO have employed a variety of compositions known in the art. For example, a cream containing 50% DMSO has been used for treating complex regional pain syndrome. For prevention of skin and tissue damage caused by chemotherapy agents leaking from the IV, a dressing containing 77% to 90% DMSO solution has been applied to the skin at the site of IV administration. For rash caused by shingles (herpes zoster), a composition of 5% to 40% idoxuridine in DMSO has been applied every 4 hours for 4 days or until the skin starts to heal. For painful bladder (interstitial cystitis) or inflammatory bladder disease, undiluted DMSO solution is administered as a drip using a catheter.

Heretofore, a topical composition comprising DMSO as the sole effective agent has not been described for treatment and cure of acne, dermatitis, rosacea, common warts, molluscum contagiosum, onychomycosis, or paronychia. More particularly, a topical gel composition comprising less than 50% DMSO and a gelling agent in aqueous solvent has not been described for treating or curing these skin diseases or conditions.

What is needed is a composition which can provide effective treatment and cure of one or more skin conditions or diseases caused by viral, bacterial or fungal infections, or complicated by secondary or opportunistic microbial colonization infection. Such composition can be advantageous for treating or curing acne, dermatitis, rosacea, common warts, molluscum contagiosum, onychomycosis, or paronychia.

BRIEF SUMMARY

The subject invention concerns a novel composition comprising dimethyl sulfoxide (DMSO) as an effective agent wherein the composition is useful for treating skin diseases or conditions caused by, associated with, or are complicated by microbial infection. It was surprisingly and unexpectedly discovered that compositions comprising DMSO, alone, without any additional antibacterial, antiviral, antifungal, antibiotic, antibacterial, antiseptic, iodine-containing, iodophor or povidone-iodine agents, are effective in treating ungual, fungal, viral, or bacterial infections of the skin.

Causative agents associated with certain skin diseases or conditions treatable using a composition of the invention include viruses, bacteria, or fungi. Skin diseases or conditions treatable using a composition of the invention include acne, common warts, dermatitis, genital warts, herpetic lesions or herpetic viral disease, molluscum contagiosum, onychomycosis, paronychia, and rosacea.

In a preferred embodiment, the composition of the invention comprises DMSO and an aqueous solvent, such as water or an isotonic buffer. In another preferred embodiment a composition of the invention comprises DMSO and a gelling agent, preferably a cellulosic gelling agent, e.g., hydroxyethyl cellulose (HEC). In a further preferred embodiment, a composition of the invention comprises DMSO, a gelling agent, and the balance being one or more diluents or solvents, preferably water or an aqueous solvent. In a more preferred embodiment, a composition of the invention comprises DMSO at a concentration of about 50% (w/v) or less, a gelling agent at a concentration of 10% (w/v) or less, and the balance being one or more solvents, preferably water or an aqueous solvent.

A composition of the subject invention can exclude, or be free of, an active antifungal, antiviral, antibacterial, or antiseptic agent known to have activity against microbial-related skin diseases or conditions, and specifically excludes or is free of an iodophor or elemental iodine-based active agents, used for its antifungal, antiviral, antibacterial, or antiseptic properties. Preferred embodiments of a topical gel composition of the invention are free of any additional API or anti-inflammatory drug, such as a steroid, e.g., corticosteroid, or non-steroidal anti-inflammatory drug (NSAID). Thus, a composition of the invention can be described as steroid-free, NSAID-free, steroid-free and NSAID-free, or anti-inflammatory-free. A composition of the invention is advantageously useful for treatment of the described conditions without an anti-inflammatory, without a steroid, or without an NSAID present in the composition.

A composition of the invention can include a second agent useful for ameliorating secondary symptoms of the condition or disease to be treated, e.g., pain, swelling, itchiness, or redness, such as an anti-inflammatory drug, a non-steroidal anti-inflammatory drug (NSAID), a steroid, a local anesthetic (e.g., lidocaine) or the like, which are not intended to directly affect or treat the causative agent. However, a preferred embodiment of a composition of the invention comprises DMSO as a single effective agent and excludes, or is free of, a second active agent. More specifically, a composition of the invention excludes or is free of a second active agent useful for directly treating a microbial causative agent of skin disease or condition.

A preferred composition comprises about 0.01% to about 10% gelling agent. A more preferred composition can comprise about 1% to about 3% gelling agent. A particularly useful composition comprises a cellulosic polymer as a gelling agent, such as hydroxyethylcellulose (HEC). A particularly useful composition which has been prepared in accordance with the subject invention comprises 44% DMSO and 2% hydroxyethylcellulose and 54% aqueous solvent. Preferred aqueous solvent is water or isotonic buffer.

In one embodiment, a composition of the subject invention can be useful for treating a skin disease and/or condition complicated by microbial colonization and/or infection.

The subject invention also includes a method of treating a skin disease, wherein the method comprises topically administering an effective amount of a composition comprising DMSO as an effective agent to provide a clinical cure of the target skin disease or condition. Preferably, the method of the subject invention comprises topically administering an effective amount of a composition comprising DMSO in an aqueous solvent, and more preferably comprises administering an effective amount of a composition comprising DMSO, a gelling agent, and an aqueous solvent.

In an embodiment, the method of the invention comprises the steps of:
  a) providing a composition comprising DMSO as an effective agent and free of an active antifungal, antiviral, antibacterial, or antiseptic agent, iodophor or elemental-iodine;
  b) topically administering an effective amount of the composition to the skin or nail of a patient suffering from a skin disease or condition caused or complicated by microbial infection one to four times per day; and
  c) optionally, repeating the topical administration of step b) for a period of two days up to about 12 weeks until the skin disease or condition is clinically cured.

An effective amount of the composition is an amount that, when applied to the skin surface of a patient, covers a target area of the skin exhibiting the symptoms or lesions caused by the skin disease or condition. The composition can be dabbed or spread onto the target area by hand, or by using an applicator.

In accordance with the subject method, a composition of the subject invention can provide a clinical cure rate of up to 40%, defined as complete resolution of all baseline lesions after 8 weeks of topical therapy.

In an embodiment, the method of the invention comprises topically administering an effective amount of a composition comprising DMSO to treat the skin disease by penetrating the outer layers of the skin. In another embodiment, the method of the invention comprises topically administering an effective amount of a composition comprising DMSO to treat the skin disease without penetrating the outer layers of the skin. In an embodiment, the composition can treat the skin disease prior to penetrating the skin. In an embodiment, the composition can treat the skin disease both by penetrating the skin and prior to penetrating the skin.

In an embodiment, disclosed herein is a composition for treating a skin disease complicated by microbial colonization and/or infection, the composition comprising a cellulosic polymer gelling agent and dimethyl sulfoxide (DMSO) wherein the composition is free of any other active antiviral agents, antiseptic compounds, and iodine-containing compounds, wherein the composition is capable of achieving a clinical cure rate defined as complete resolution of the skin disease in at least 40% of treated patients within eight weeks of topical administration of an effective amount of the subject composition once per day, and up to four times per day. In an embodiment, the cellulosic polymer is selected from the group consisting of methylcellulose, ethyl cellulose, carboxymethylcellulose, hydroxypropyl methylcellulose, or hydroxyethylcellulose.

In an embodiment, a composition disclosed herein for treatment of a skin disease complicated by microbial colonization and/or infection is substantially anhydrous. In an embodiment, the composition is anhydrous. In another embodiment the composition contains water.

In an embodiment, the skin disease or condition treated is a fungal infection. In an embodiment, the skin disease or condition treated is caused by a dermatophyte infection. In an embodiment, the skin disease or condition treated is caused by a bacterial infection. In an embodiment, the skin disease or condition treated is caused by a viral infection. In an embodiment, the skin disease or condition treated is caused by a viral infection of molluscum contagiosum virus. In an embodiment, the skin disease or condition treated is caused by a viral infection of herpes virus. In an embodiment, the skin disease or condition treated is caused by a viral infection of human papilloma virus (HPV).

In an embodiment, disclosed herein is a method for treating a skin or nail disease complicated by microbial colonization and/or infection, comprising contacting an affected area of the skin with a composition disclosed herein and repeating the contacting step as necessary until the skin disease has been treated. In an embodiment, the contacting step is conducted at least once a day. In an embodiment, the skin disease is dermatitis. In an embodiment, the skin disease is rosacea. In an embodiment, the skin disease is acne. In an embodiment, the skin disease is molluscum contagiosum. In an embodiment, the skin disease is Verruca vulgaris.

In an embodiment, disclosed herein is a method of treating a skin disease or condition complicated by microbial colonization and/or infection, comprising contacting an affected area of the skin or nail with a composition disclosed herein at least one time per day and repeating the contacting step for at least four weeks. In an embodiment, disclosed herein is a method of treating a skin disease complicated by microbial colonization and/or infection, comprising contacting an affected area of the skin or nail with a composition disclosed herein and repeating the contacting step for at least six weeks. In an embodiment, disclosed herein is a method of treating a skin disease complicated by microbial colonization and/or infection, comprising contacting an affected area of the skin or nail with a composition disclosed herein at least one time per day and repeating the contacting step for at least eight weeks. In an embodiment, disclosed herein is a method of treating a skin disease complicated by microbial colonization and/or infection, comprising contacting an affected area of the skin or nail with a composition disclosed herein at least one time per day and repeating the contacting step for at least 12 weeks.

The subject invention further concerns a method for treating, or inhibiting the growth of, warts, including genital warts, caused by human papilloma virus (HPV) or molluscum contagiosum virus (MCV). The method comprises, generally, one or more as needed administrations or topical applications of a topical gel of the invention, namely, a topical composition comprising DMSO and a gelling agent, to the site, until the wart is eliminated, or its growth is substantially inhibited. In a preferred method, the subject gel composition is administered directly onto the wart or affected area as needed (PRN), preferably at least once per day (QD), or more preferably at least two times per day (BID) until results are seen, typically for about one week, up to about 24 weeks.

More particularly, a method of the subject invention comprises treating an infection of the skin, including skin of genitalia, by providing a composition as described herein, and applying an effective amount of a topical gel composition to a site of the infection as needed to reduce or eliminate the infection caused by or associated with one or more infectious agents selected from the group consisting of bacteria, demodex, fungus or yeast, and virus.

DETAILED DESCRIPTION

The subject invention concerns a novel topical pharmaceutical composition comprising DMSO as an effective agent wherein the composition is useful for treating skin diseases or conditions caused by, associated with, or are complicated by microbial infection. It was surprisingly and unexpectedly discovered that a composition comprising DMSO, alone, without a second or additional antibacterial, antiviral, antifungal, antibiotic, antibacterial, antiseptic, iodine-containing, iodophor or povidone-iodine agent, also referred to herein as excluding a second active ingredient or being free of a second or additional antimicrobial, antiviral, antibacterial or antiseptic agent, is effective in treating ungual infection or fungal, viral, or bacterial infections of the skin.

It was surprisingly found that a composition comprising DMSO in an aqueous solvent, and a gelling agent, such as a cellulosic polymer, but without any additional antibacterial, antiviral, antifungal, antibiotic, antibacterial, antiseptic, iodine-containing, iodophor or povidone-iodine agent, is effective in treating fungal, viral, and bacterial infection of the skin or nail such as acne, dermatitis, rosacea, common warts, molluscum contagiosum, onychomycosis, or paronychia.

Although known as a penetration enhancer for small molecules, including certain antiviral or antibacterial active pharmaceutical ingredients, DMSO has not heretofore been described as having antimicrobial or antiviral activity for treating skin conditions or diseases caused by a microbial infection or complicated by a secondary microbial infection. Compositions comprising DMSO without additional antimicrobial, antiviral, antibacterial or antiseptic components, have now unexpectedly been demonstrated to effectively treat viral skin infections, including molluscum contagiosum and verruca vulgaris.

In another aspect, as further described herein, it was surprisingly found that a composition comprising DMSO, a cellulosic polymer as a gelling agent, in an aqueous solvent, but without, or free of, additional known antimicrobial, antiviral, antifungal or antiseptic agents could be used to treat skin and nail disease. Preferred embodiments of a topical gel composition of the invention are free of any additional API or anti-inflammatory drug, such as a steroid, e.g., corticosteroid, or non-steroidal anti-inflammatory drug (NSAID). Thus, a composition of the invention can be described as steroid-free, NSAID-free, steroid-free and NSAID-free, or anti-inflammatory-free. A composition of the invention is advantageously useful for treatment of the described conditions without an anti-inflammatory, without a steroid, or without an NSAID present in the composition.

In an embodiment, compositions containing DMSO and cellulosic polymer, but not containing any additional antibiotics, antivirals, antiseptics including povidone-iodine or other iodophors, were shown to be effective for the treatment of molluscum contagiosum.

A composition of the invention can include a gelling agent, as well-known in the pharmaceutical art, selected from a gum, agar, carrageenan, petrolatum, or a cellulosic polymer or the like. One preferred cellulosic polymer as a gelling agent is hydroxyethyl cellulose (HEC). An alternative cellulosic polymer gelling agent is hydroxymethyl cellulose (HMC). Alternative cellulosic polymers that can be employed in the composition include ethyl cellulose, methylcellulose, ethyl methyl cellulose, hydroxyethyl cellulose, hydroxypropyl cellulose, hydroxyethyl methyl cellulose, hydroxypropyl methylcellulose, ethyl hydroxyethyl cellulose and carboxymethyl cellulose.

In an embodiment, a composition comprises cellulosic polymer in the range of about 0.01% to about 10%. In another embodiment, a composition comprises cellulosic polymer in the range between 0.1% and 5%. In another embodiment, a composition comprises cellulosic polymer in the range between 0.5% and 4%. In another embodiment, a composition comprises cellulosic polymer in the range between 1% and 3%. In another embodiment, a composition comprises cellulosic polymer in the range between 1.5% and 2.5%. In another embodiment, a composition comprises cellulosic polymer in the range between greater than 1.5% and less than 2.5%. In another embodiment, a composition comprises cellulosic polymer in the range of less than 2.5%. In another embodiment, a composition comprises cellulosic polymer in the range of less than 2.1%. In another embodiment, a composition comprises cellulosic polymer in the range of about 2%, or can comprise 2.0% cellulosic polymer.

The present invention concerns a topical gel composition comprising DMSO and a gelling agent. The composition can, optionally, further comprise a lubricant or co-solvent, or other pharmaceutically acceptable excipients. For example, a composition for treating a skin disease or condition can include a pharmaceutically acceptable excipient. A composition for treating an ophthalmic condition, such as blepharitis can include an excipient which is pharmaceutically acceptable and ophthalmically acceptable.

A specific but non-limiting example of a formulation of the invention providing a useful pharmaceutical preparation comprises DMSO with water and one or more co-solvents in solution and prepared as a gel or semi-solid.

In another embodiment, DMSO can be added to aqueous solutions of HEC. In an example DMSO can be present as a co-solvent with water in the range of 1%-99%. One embodiment of such a formulation could include a range of excipients such as sodium chloride, sodium dihydrogen phosphate monohydrate, disodium hydrogen phosphate anhydrous and water, as well as others known to those skilled in the art. C1-C4 alcohols can be included in the composition with the understanding that alcohols may be less preferred for ophthalmic compositions due to stinging sensation that may occur when coming into contact with the eye.

A preferred method of treating viral infection of the skin or genitalia comprises administration or application to a skin infection caused by or associated with human papilloma virus (HPV) or molluscum contagiosum virus (MCV).

Preferably, the subject method can be used to reduce or eliminate a viral wart. The method can be carried out by application or administration of the composition to a skin infection on the skin of the face or genitalia.

Yet another aspect of the invention comprises a method of treating an infectious condition of the periocular skin, comprising applying an effective amount of a stable, topical ophthalmic gel composition to a site of the infection to reduce or eliminate the infection in or around the eyelid. The method of the invention can be useful in treating blepharitis, conjunctivitis, corneal ulcer, HSV keratitis, conjunctival neoplasia, AC inflammation, post-operative endophthalmitis, and endophthalmitis after intravitreal or intracameral injection, which is caused by or associated with one or more infectious agents such as bacteria, demodex, fungus or yeast, or virus.

The subject composition is surprisingly useful for the treatment of viral wart infection of the skin, as well as viral, demodex, fungal/yeast or bacterial infection of the eyelids, Meibomian glands, which can cause blepharitis.

In another aspect, as further described herein, is was surprisingly found that the compositions and methods encompassed herein are useful for treating conditions in addition to ungual fungal infections, including, but not limited to, other fungal infections, yeast infections, viral infections, and bacterial infections, including both gram positive and Gram-negative bacteria.

In an aspect, as further described herein, it was surprisingly found that the compositions and methods encompassed herein are useful for treating paronychia. In an aspect, the compositions and methods encompassed herein are useful for treating skin diseases complicated by microbial colonization and/or infection.

Contemplated herein are compositions comprising at least DMSO, water and at least one cellulosic polymer agent but not comprising, or excluding or being free of, any povidone-iodine or any other antimicrobial, antiseptic, antiviral or antibacterial active agents, for the treatment of ungual fungal infections, and methods of using the same. Also contemplated herein are compositions comprising at least DMSO and at least one cellulosic polymer agent but not comprising any povidone-iodine or any other antimicrobial, antiseptic, antiviral or antibacterial active agents, for the treatment of skin diseases complicated by microbial colonization and/or infection.

Therapeutic Indications

In an embodiment, disclosed herein are compositions and methods for treating skin diseases. In an embodiment, disclosed herein are compositions and methods for treating skin diseases complicated by microbial colonization and/or infection. In an embodiment, disclosed herein are compositions and methods for treating skin diseases caused primarily by viruses. In an embodiment, disclosed herein are compositions and methods for treating skin diseases associated with cancer chemotherapy treatment including paronychia, nail dystrophy, acneiform rash and dermatitis. Examples of such conditions and/or diseases include, but are not limited to, Molluscum contagiosum, seborrheic dermatitis, hand dermatitis, atopic dermatitis, acne, rosacea, and Verruca vulgaris. In an embodiment, the composition is used to treat the skin disease by penetrating the skin. In an embodiment, the composition is used to treat the skin disease without penetrating the skin. In an embodiment, the composition is used to treat the skin disease prior to penetrating the skin. In an embodiment, the composition is used to treat the skin disease both by penetrating the skin and prior to penetrating the skin.

In an embodiment, disclosed herein are compositions and methods for treating onychomycosis, or nail (ungual) fungal infection. Therefore, the compositions and methods are useful for treatment of the unguis, or ungual surfaces, areas adjacent to or contact the unguis, or areas nearby an ungual surface. In an embodiment, the compositions and methods herein treat infections located in one or more of the unguis, the subungual space, and the periungual space. The compositions and methods are further useful in treating any combination of the above.

The term "treating", as used herein, refers to a detectable improvement in an adverse condition and/or a lessening the symptoms of the condition upon contacting a mammal with a composition disclosed or encompassed by the disclosure herein. The term "treating" encompasses both a partial improvement in an adverse condition and a complete eradication (i.e., "cure") of the condition. In an aspect, an infection is treated.

As the term is used herein, an "affected" area of the skin is an area of the skin involved in the disease state or adverse condition. By way of a non-limiting example, an affected area of the skin in a case of hand dermatitis includes skin on, around, or near the hand that demonstrates one or more signs, symptoms, characteristics, or properties of a dermatitis condition as would be understood by the skilled artisan.

The term "topical" or "topical administration" means cutaneous application to an epidermal layer of skin, and, unless specifically designated, does not refer to application to mucous membrane or skin that has been debrided or surgically manipulated to open or remove the outer layer of epidermis prior to administration of the medicament.

The compositions and methods are useful for treatment of infections involving, but not limited to, dermatophytes, Candida, and nondermatophytic molds. The compositions and methods are useful for treating infections involving Trichophyton rubrum, T. mentagrophytes, Epidermophyton floccosum, T. violaceum, Microsporum gypseum, T. tonsurans, T. soudanense, T. verrucosum, as well as Neoscytalidium, Scopulariopsis, and Aspergillus.

The compositions can also be used to treat virtually any kind of fungal and/or mycotic pathogens (some of which are described in Scrip's Antifungal Report (1992)) responsible for a variety of diseases in humans, ranging from mycoses involving unguis, skin, hair, or mucous membranes, further including, but not limited to, Absidia spp., Actinomadura madurae, Actinomyces spp., Allescheria boydii, Alternaria spp., Anthopsis deltoidea, Apophysomyces elegans, Arnium leoporinum, Aspergillus spp., Aureobasidiun pullulans, Basidiobolus ranarum, Bipolaris spp., Blastomyces dermatitidis, Candida spp., Cephalosporium spp., Chaetoconidium spp., Chaetomium spp., Cladosporium spp., Coccidioides immitis, Conidiobolus spp., Corynebacterium tenuis, Cryptococcus spp., Cunninghamella bertholletiae, Curvularia spp., Dactylaria spp., Epidermophyton spp., Epidermophyton floccosum, Exserophilum spp., Exophiala spp., Fonsecaea spp., Fusarium spp., Geotrichum spp., Helminthosporium spp., Histoplasma spp., Lecythophora spp., Madurella spp., Malassezia furfur, Microsporum spp., Mucor spp., Mycocentrospora acerina, Nocardia spp., Paracoccidioides brasiliensis, Penicillium spp., Phaeosclera dematioides, Phaeoannellomyces spp., Phialemonium obovatum, Phialophora spp., Phoma spp., Piedraia hortai, Pneumocystis carinii, Pythium insidiosum, Rhinocladiella aquaspersa, Rhizomucor pusillus, Rhizopus spp., Saksenaea vasiformis, Sarcinomyces phaeomuriformis, Sporothrix schenckii, Syncephalastirum racemosuin, Taeniolella boppii, Torulopsosis spp., Trichophyton spp., Trichosporon spp., Ulocladium chartarum, Wangiella dermatitidis, Xylohypha spp., Zygomyetes spp., Tinea barbae, Tinea capitis, Tinea corporis, Tinea cruris, Tinea favosa, Tinea imbricata, Tinea manuum, Tinea nigra (palmalis), Tinea pedis, Tinea unguium, Torulopsosis, Trichomycosis axillaris, White piedra. Such organisms are responsible for conditions and infections such as, but not limited to Otitis externa (otomycosis), Actinomycosis, Aspergillosis, Candidiasis, Chromomycosis, Coccidioidomycosis, Cryptococcosis, Entomophthoramycosis, Geotrichosis, Histoplasmosis, Mucormycosis, Mycetoma, Nocardiosis, North American Blastomycosis, Paracoccidioidomycosis, Phaeohyphomycosis, Phycomycosis, pneumocystic pneumonia, Pythiosis, Sporotrichosis, and Torulopsosis. Other fungi that have pathogenic potential include, but are not limited to, Thermomucor indicae-seudaticae, Radiomyces spp., and other species of known pathogenic genera. These fungal organisms are ubiquitous in air, soil, food, decaying food, etc.

In an embodiment, treatment of a patient using the compositions and methods encompassed herein may also treat a viral and/or bacterial infection as a fungal or mycotic infection is being treated in a patient. In an embodiment, treatment of a patient using the compositions and methods encompassed herein may be deliberately used to treat a viral and/or bacterial infection in a patient, apart from treatment of a fungal or mycotic infection in a patient.

By way of non-limiting examples, herpes simplex virus (HSV) and human papilloma virus (HPV) can be treated according to the methods and/or compositions disclosed herein. By way of another non-limiting example, an inguinal infection or condition can be treated according to the methods and/or compositions disclosed herein. By way of non-limiting examples, molluscum contagiosum virus (MCV) and human papilloma virus (HPV) can be treated according to the methods and/or compositions disclosed herein.

In an embodiment, the compositions and methods encompassed herein can be used to treat paronychia. Paronychia is an infection of the soft tissue surrounding the unguis and may be associated with an ungual infection. Paronychia may involve infections of one or more of fungal, bacterial, and yeast origins. In an embodiment, compositions and/or methods encompassed herein are also useful for treating one or more of—but not limited to—verrucous warts, molluscum contagiosum, non-genital herpes simplex, scars, healing wounds, gram negative toe-web infection, psoriatic nail dystrophy, and tinea pedis. In an embodiment, such treatment encompasses treating the infection or infections present.

The compositions and methods are useful in treating one or any combination of at least two of the above diseases, conditions or pathogens.

Compositions

In an embodiment, a composition comprises at least DMSO and a diluent. The diluent can be a solvent and is preferably an aqueous solvent such as water or an isotonic aqueous buffer. The composition can comprise one or more additional solvents or co-solvents. A composition of the invention does not contain povidone-iodine or other iodine-containing agent and excludes a bleaching agent such as chlorine or chloride compounds, and further excludes or is free of, a second or additional antibacterial, antiviral, antibiotic, antiseptic or antifungal compound or agent.

In one embodiment, the composition of the invention can comprise DMSO as the sole effective agent, an aqueous solvent or water, and a gelling agent. A preferred gelling agent is a cellulosic polymer. A composition of the invention can comprise one or more other or additional inactive ingredients selected from the United States Food and Drug Administration (FDA) list of approved inactive ingredients. A composition of the invention does not contain inactive ingredients or excipients not listed in the FDA list of approved inactive ingredients. A composition of the invention does not comprise, excludes, or is free of, elemental iodine or iodine salt, povidone-iodine, other iodophor or iodine-containing agent, any halogen bleaching agents such as chlorine and the like, any antibacterial, antiviral, antibiotic, antiseptic or antifungal compounds or agents.

In an embodiment, a composition can comprise one or more naturopathic substances. Naturopathic substances include, but are not limited to, Punica Granatum (Pomegranate) Extract, Camellia Sinensis Leaf (Green Tea) Extract, Ascorbic Acid (Vitamin-C), Calendula Officinalis Extract, Glycrrhiza Glabra (Licorice) Extract, Allantoin, and Cucumis Sativus (Cucumber) Fruit Extract. In an embodiment, a composition comprises DMSO, PVP-I, Punica Granatum (Pomegranate) Extract, Camellia Sinensis Leaf (Green Tea) Extract, Ascorbic Acid (Vitamin-C), Calendula Officinalis Extract, Glycrrhiza Glabra (Licorice) Extract, Allantoin, and Cucumis Sativus (Cucumber) Fruit Extract.

In an embodiment, DMSO can comprise the sole solvent in the composition. In an embodiment, DMSO is one part of a solvent mixture that can contain water, other solvents, non-aqueous solvents and/or cellulosic polymeric gel forming agents.

In an embodiment, a composition comprises DMSO as an effective agent for treating a microbial infection of the skin. In another embodiment, a composition consists essentially of DMSO, HEC and a solvent. In yet another embodiment, a composition consists of DMSO, HEC, and water.

In an embodiment, a composition comprises at least one co-solvent. In an embodiment, a composition comprises DMSO as a primary solvent, and further comprises at least one co-solvent. In an embodiment, water is a co-solvent. In an embodiment, a composition comprises DMSO as the primary solvent and water as a co-solvent. In an embodiment, a composition consists of DMSO as the primary solvent and water as the co-solvent. In another embodiment, a composition consists essentially of DMSO as the primary solvent and water as the co-solvent. In an embodiment, a composition comprises at least one co-solvent such as, but not limited to, water, or ethanol. In an embodiment, a co-solvent is one or more polar aprotic solvent. One of skill in the art will understand the advantages and limitations of the use of co-solvents, based on the properties and physical effects of such potential co-solvents, in view of the disclosure set forth herein. Other co-solvents are described in greater detail elsewhere herein.

In an embodiment, a composition comprises at least one excipient such as, but not limited to, sodium chloride, sodium dihydrogen phosphate monohydrate, disodium hydrogen phosphate anhydrous and water. The compositions encompassed herein will be understood to optionally include one or more other excipients as known to those skilled in the art. One of skill in the art will know how to identify such an excipient as useful in the present compositions and methods, for example, when such an excipient enhances the therapeutic effectiveness, stability, or potency of a composition or method. Other excipients are presented in greater detail elsewhere herein.

In an embodiment, a composition comprises at least one preservative. Preservatives include, but are not limited to, chlorine dioxide, quaternary ammonium compounds, such as benzalkonium chloride, benzethonium chloride, cetrimide, dequalinium chloride, and cetylpyridinium chloride; mercurial agents, such as phenylmercuric nitrate, phenylmercuric acetate, and thimerosal; alcoholic agents, for example, chlorobutanol, phenylethyl alcohol, and benzyl alcohol; antibacterial esters, for example, esters of parahydroxybenzoic acid; and other anti-microbial agents such as chlorhexidine, chlorocresol, benzoic acid and polymyxin. In one embodiment, the composition is preservative-free and self-preserved. In another embodiment, the composition is non-preserved.

Dosages, Forms and Formulations

As used herein, a "pharmaceutically acceptable" component of a composition of the invention includes any and all solvents, dispersion media, coatings, surfactants, antioxidants, isotonic agents, absorption delaying agents, salts, preservatives, drugs, drug stabilizers, gels, binders, excipients, disintegration agents, lubricants, sweetening agents, flavoring agents, dyes, such like materials and combinations thereof, as would be known to one of ordinary skill in the art (see, for example, Remington's Pharmaceutical Sciences, 1990, incorporated herein by reference). Except insofar as any conventional component is incompatible with the DMSO solvent or method of use, its use in the pharmaceutical compositions is contemplated.

Percentages set forth herein are (w/w), with respect to the specified component in the overall composition, unless otherwise indicated.

In an embodiment, anhydrous DMSO is used in a composition. In an embodiment, substantially anhydrous DMSO is used in a composition. It will be understood by one of skill in the art that DMSO can be produced and/or obtained in differing grades, and that one of the variables among DMSO preparations of different grades is the water content. By way of example, DMSO may be completely anhydrous (also referred to herein simply as "anhydrous"), substantially anhydrous, or may contain water to a measurable degree. It will be understood that the amount of measurable water in a DMSO preparation may vary based on limitations of the instrumentation and techniques used to make such measurements. In an embodiment, DMSO that is not completely anhydrous may be substantially anhydrous and contain water at a level below levels of detectability.

In an embodiment, DMSO that is not completely anhydrous may contain water, wherein the water content is about at least 0.01%, about at least 0.02%, about at least 0.03%>, about at least 0.04%>, about at least 0.05%>, about at least 0.06%>, about at least 0.07%), about at least 0.08%>, about at least 0.09%>, about at least 0.1%, about at least 0.2%>, about at least 0.3%>, about at least 0.4%>, about at least 0.5%>, about at least 0.6%>, about at least 0.7%>, about at least 0.8%, about at least 0.9%, about at least 1.0%, about at least 1.5%, about at least 2.0%), about at least 2.5%, about at least 5%, about at least 7.5%, about at least 10%, about at least 12.5%, or greater. In an embodiment, DMSO that is not completely anhydrous may contain water, wherein the water content is about less than 0.01%, about less than 0.02%, about less than 0.03%), about less than 0.04%, about less than 0.05%, about less than 0.06%, about less than 0.07%), about less than 0.08%, about less than 0.09%, about less than 0.1%, about less than 0.2%, about less than 0.3%, about less than 0.4%, about less than 0.5%, about less than 0.6%, about less than 0.7%, about less than 0.8%, about less than 0.9%, about less than 1.0%, about less than 1.5%, about less than 2.0%, about less than 2.5%, about less than 5%, about less than 7.5%, about less than 10%, about less than 12.5%, or greater. It will be understood that DMSO may contain one or more other impurities in addition to water.

In an embodiment, a composition comprises DMSO which comprises water, wherein the water content is about at least 0.01%, about at least 0.02%, about at least 0.03%, about at least 0.04%, about at least 0.05%, about at least 0.06%, about at least 0.07%, about at least 0.08%, about at least 0.09%, about at least 0.1%), about at least 0.2%, about at least 0.3%, about at least 0.4%, about at least 0.5%, about at least 0.6%, about at least 0.7%, about at least 0.8%, about at least 0.9%, about at least 1.0%, about at least 1.5%, about at least 2.0%, about at least 2.5%, about at least 5%, about at least 7.5%, about at least 10%, about at least 12.5%, or greater. In an aspect, the water may be derived from a component of the composition. In another aspect, the water may be specifically added to the composition.

In an embodiment, a composition comprises at least one of United States Pharmacopeia Convention (USP) grade DMSO, Active Pharmaceutical Ingredient (API) grade DMSO, analytical grade DMSO, and American Chemical Society (ACS) Spectrophotometric grade DMSO. In an embodiment, a composition comprises DMSO having <0.1% water by KF titration and >99.9% determined on an anhydrous basis.

As set forth above, the percent amount of all ingredients of the composition, including DMSO or gelling agent or solvent, are described in a weight-to-weight (w/w) ratio with respect to one or more other components of the composition, unless otherwise indicated.

In an embodiment, a composition comprises DMSO in the range of 0.1% to 99.99%. In an embodiment, a composition comprises DMSO in the range of 1% to 99.9%. In another embodiment, a composition comprises DMSO in the range of 5% and 99.9%. In another embodiment, a composition comprises DMSO in the range of 10% and 99.9%. In another embodiment, a composition comprises DMSO in the range of 20% and 99.9%. In another embodiment, a composition comprises DMSO in the range of 30% and 99.9%. In another embodiment, a composition comprises DMSO in the range of 40% and 99.9%. In another embodiment, a composition comprises DMSO in the range of 50% and 99.9%. In another embodiment, a composition comprises DMSO in the range of 60% and 99.9%. In another embodiment, a composition comprises DMSO in the range of 70% and 99.9%. In another embodiment, a composition comprises DMSO in the range of 80% and 99.9%, and in yet another embodiment, between 90% and 99.9%, In an embodiment, a composition comprises DMSO at about at least 1%. In other embodiments, a composition comprises DMSO at about 2%, about 3%, about 4%, about 5%, about 6%, about 7%, about 8%, about 9%, about 10%, about 11%, about 12%, about 13%, about 14%, about 15%, about 16%, about 17%, about 18%, about 19%, about 20%, about 21%, about 21%, about 22%, about 23%, about 24%, about 25%, about 26%, about 27%, about 28%, about 29%, about 30%, about 31%, about 32%, about 33%, about 34%, about 35%, about 36%, about 37%, about 38%, about 39%, about 40%, about 41%, about 42%, about 43%, about 44%, about 45%, about 46%, about 47%, about 48%, about 49%, about 50%, about 51%, about 52%, about 53%, about 54%, about 55%, about 56%, about 57%, about 58%, about 59%, about 60%, about 61%), about 62%), about 63%, about 64%, about 65%, about 66%, about 67%, about 68%, about 69%, about 70%, about 71%, about 72%, about 73%, about 74%, about 75%, about 76%, about 77%, about 78%, about 79%, about 80%, about 81%, about 82%, about 83%, about 84%, about 85%, about 86%, about 87%, about 88%, about 89%, about 90%, about 91%, about 92%, about 93%, about 94%, about 95%, about 96%, about 97%, about 98%, about 99%, about 99.5%, or about 99.9%.

In an embodiment, a composition comprises DMSO in weight percent in the range having a lower limit of 0.1% and an upper limit of 99.99%. The lower limit of the range of DMSO in the composition can be 1.0%, 1.5%, 2.0%, 2.5%, 3.0%, 3.5%, 4.0%, 4.5%, 5.0%, 5.5%, 6.0%, 6.5%, 7.0%, 7.5%, 8.0%, 8.5%, 9.0%, 9.5%, 10.0%, 10.5%, 11.0%, 11.5%, 12.0%, 12.5%, 13.0%, 13.5%, 14.0%, 14.5%, 15.0%, 15.5%, 16.0%, 16.5%, 17.0%, 17.5%, 18.0%, 18.5%, 19.0%, 19.5%, 20.0%, 20.5%, 21.0%, 21.5%, 22.0%, 22.5%, 23.0%, 23.5%, 24.0%, 24.5%, 25.0%, 25.5%, 26.0%, 26.5%, 27.0%, 27.5%, 28.0%, 28.5%, 29.0%, 29.5%, 30.0%, 30.5%, 31.0%, 31.5%, 32.0%, 32.5%, 33.0%, 33.5%, 34.0%, 34.5%, 35.0%, 35.5%, 36.0%, 36.5%, 37.0%, 37.5%, 38.0%, 38.5%, 39.0%, 39.5%, 40.0%, 40.5%, 41.0%, 41.5%, 42.0%, 42.5%, 43.0%, 43.5%, 44.0%, 44.5%, 45.0%, 45.5%, 46.0%, 46.5%, 47.0%, 47.5%, 48.0%, 48.5%, 49.0%, 49.5%, 50.0%, 50.5%, 51.0%, 51.5%, 52.0%, 52.5%, 53.0%, 53.5%, 54.0%, 54.5%, 55.0%, 55.5%, 56.0%, 56.5%, 57.0%, 57.5%, 58.0%, 58.5%, 59.0%, 59.5%, 60.0%, 60.5%, 61.0%, 61.5%, 62.0%, 62.5%, 63.0%, 63.5%, 64.0%, 64.5%, 65.0%, 65.5%, 66.0%, 66.5%, 67.0%, 67.5%, 68.0%, 68.5%, 69.0%, 69.5%, 70.0%, 70.5%, 71.0%, 71.5%, 72.0%, 72.5%, 73.0%, 73.5%, 74.0%, 74.5%, 75.0%, 75.5%, 76.0%, 76.5%, 77.0%, 77.5%, 78.0%, 78.5%, 79.0%, 79.5%, 80.0%, 80.5%, 81.0%, 81.5%, 82.0%, 82.5%, 83.0%, 83.5%, 84.0%, 84.5%, 85.0%, 85.5%, 86.0%, 86.5%, 87.0%, 87.5%, 88.0%, 88.5%, 89.0%, 89.5%, 90.0%, 90.5%, 91.0%, 91.5%, 92.0%, 92.5%, 93.0%, 93.5%, 94.0%, 94.5%, 95.0%, 95.5%, 96.0%, 96.5%, 97.0%, 97.5%, 98.0%, 98.5%, 99.0%, or 99.5%.

The upper limit of the range of DMSO in the composition can be 1.5%, 2.0%, 2.5%, 3.0%, 3.5%, 4.0%, 4.5%, 5.0%, 5.5%, 6.0%, 6.5%, 7.0%, 7.5%, 8.0%, 8.5%, 9.0%, 9.5%, 10.0%, 10.5%, 11.0%, 11.5%, 12.0%, 12.5%, 13.0%, 13.5%, 14.0%, 14.5%, 15.0%, 15.5%, 16.0%, 16.5%, 17.0%, 17.5%, 18.0%, 18.5%, 19.0%, 19.5%, 20.0%, 20.5%, 21.0%, 21.5%, 22.0%, 22.5%, 23.0%, 23.5%, 24.0%, 24.5%, 25.0%, 25.5%, 26.0%, 26.5%, 27.0%, 27.5%, 28.0%, 28.5%, 29.0%, 29.5%, 30.0%, 30.5%, 31.0%, 31.5%, 32.0%, 32.5%, 33.0%, 33.5%, 34.0%, 34.5%, 35.0%, 35.5%, 36.0%, 36.5%, 37.0%, 37.5%, 38.0%, 38.5%, 39.0%, 39.5%, 40.0%, 40.5%, 41.0%, 41.5%, 42.0%, 42.5%, 43.0%, 43.5%, 44.0%, 44.5%, 45.0%, 45.5%, 46.0%, 46.5%, 47.0%, 47.5%, 48.0%, 48.5%, 49.0%, 49.5%, 50.0%, 50.5%, 51.0%, 51.5%, 52.0%, 52.5%, 53.0%, 53.5%, 54.0%, 54.5%, 55.0%, 55.5%, 56.0%, 56.5%, 57.0%, 57.5%, 58.0%, 58.5%, 59.0%, 59.5%, 60.0%, 60.5%, 61.0%, 61.5%, 62.0%, 62.5%, 63.0%, 63.5%, 64.0%, 64.5%, 65.0%, 65.5%, 66.0%, 66.5%, 67.0%, 67.5%, 68.0%, 68.5%, 69.0%, 69.5%, 70.0%, 70.5%, 71.0%, 71.5%, 72.0%, 72.5%, 73.0%, 73.5%, 74.0%, 74.5%, 75.0%, 75.5%, 76.0%, 76.5%, 77.0%, 77.5%, 78.0%, 78.5%, 79.0%, 79.5%, 80.0%, 80.5%, 81.0%, 81.5%, 82.0%, 82.5%, 83.0%, 83.5%, 84.0%, 84.5%, 85.0%, 85.5%, 86.0%, 86.5%, 87.0%, 87.5%, 88.0%, 88.5%, 89.0%, 89.5%, 90.0%, 90.5%, 91.0%, 91.5%, 92.0%, 92.5%, 93.0%, 93.5%, 94.0%, 94.5%, 95.0%, 95.5%, 96.0%, 96.5%, 97.0%, 97.5%, 98.0%, 98.5%, 99.0%, or 99.5%.

In a preferred embodiment, a composition of the invention comprises about 60% or less of DMSO, or comprises about 55% or less DMSO, or comprises about 50% or less DMSO or comprises about 45% or less DMSO. A preferred composition comprises from about 10% to about 60% DMSO, from about 20% to about 50% DMSO, from about 30% DMSO to about 49% DMSO, from about 40% to about 48% DMSO, from about 41% to about 47% DMSO, from about 42% to about 46% DMSO, from about 43% to about 45% DMSO, or about 44% DMSO.

In an embodiment, a composition comprises DMSO but does not comprise any additional solvent (e.g., co-solvent)

or penetrant. In another embodiment, a composition comprises DMSO in the range of about 0.01% to 99.99% and further comprises at least one co-solvent including, for example, water, in the range of 0.01% to about 99.99%. In an embodiment, a composition comprises DMSO and further comprises at least one co-solvent in the range of about 0.1% to about 50%. In another embodiment, a composition comprises DMSO and further comprises at least one co-solvent in the range between about 5% and about 50%. In another embodiment, a composition comprises DMSO and further comprises at least one co-solvent in the range between about 10% and about 99%. In another embodiment, a composition comprises DMSO and further comprises at least one co-solvent in the range between about 20% and about 95%. In an embodiment, a composition comprises DMSO and further comprises at least one co-solvent in the range of about 50% to about 60%, about 60% to about 80%, about 70% to about 90%, and about 80% to about 95%. In an aspect, water is a co-solvent. In an embodiment, a composition comprises DMSO, water, and at least one additional co-solvent. In an embodiment, a composition comprises DMSO, water, and at least two additional co-solvents. In an embodiment, a composition is substantially anhydrous and comprises DMSO and at least one additional co-solvent.

In an embodiment, a composition comprises a co-solvent in the range of 1% to 99.99%. In another embodiment, a composition comprises a co-solvent in the range of 5% and 99.9%. In another embodiment, a composition comprises a co-solvent in the range of 10% and 99.9%. In another embodiment, a composition comprises a co-solvent in the range of 20% and 99.9%. In another embodiment, a composition comprises a co-solvent in the range of 30% and 99.9%. In another embodiment, a composition comprises a co-solvent in the range of 40% and 99.9%. In another embodiment, a composition comprises a co-solvent in the range of 50% and 99.9%. In another embodiment, a composition comprises a co-solvent in the range of 60% and 99.9%. In another embodiment, a composition comprises a co-solvent in the range of 70% and 99.9%. In another embodiment, a composition comprises a co-solvent in the range of 80% and 99.9%), and in yet another embodiment, between 90% and 99.9%.

In an embodiment, a composition comprises a co-solvent at about 1%. In other embodiments, a composition comprises a co-solvent at about 1.0%, 1.5%, 2.0%, 2.5%, 3.0%, 3.5%, 4.0%, 4.5%, 5.0%, 5.5%, 6.0%, 6.5%, 7.0%, 7.5%, 8.0%, 8.5%, 9.0%, 9.5%, 10.0%, 10.5%, 11.0%, 11.5%, 12.0%, 12.5%, 13.0%, 13.5%, 14.0%, 14.5%, 15.0%, 15.5%, 16.0%, 16.5%, 17.0%, 17.5%, 18.0%, 18.5%, 19.0%, 19.5%, 20.0%, 20.5%, 21.0%, 21.5%, 22.0%, 22.5%, 23.0%, 23.5%, 24.0%, 24.5%, 25.0%, 25.5%, 26.0%, 26.5%, 27.0%, 27.5%, 28.0%, 28.5%, 29.0%, 29.5%, 30.0%, 30.5%, 31.0%, 31.5%, 32.0%, 32.5%, 33.0%, 33.5%, 34.0%, 34.5%, 35.0%, 35.5%, 36.0%, 36.5%, 37.0%, 37.5%, 38.0%, 38.5%, 39.0%, 39.5%, 40.0%, 40.5%, 41.0%, 41.5%, 42.0%, 42.5%, 43.0%, 43.5%, 44.0%, 44.5%, 45.0%, 45.5%, 46.0%, 46.5%, 47.0%, 47.5%, 48.0%, 48.5%, 49.0%, 49.5%, 50.0%, 50.5%, 51.0%, 51.5%, 52.0%, 52.5%, 53.0%, 53.5%, 54.0%, 54.5%, 55.0%, 55.5%, 56.0%, 56.5%, 57.0%, 57.5%, 58.0%, 58.5%, 59.0%, 59.5%, 60.0%, 60.5%, 61.0%, 61.5%, 62.0%, 62.5%, 63.0%, 63.5%, 64.0%, 64.5%, 65.0%, 65.5%, 66.0%, 66.5%, 67.0%, 67.5%, 68.0%, 68.5%, 69.0%, 69.5%, 70.0%, 70.5%, 71.0%, 71.5%, 72.0%, 72.5%, 73.0%, 73.5%, 74.0%, 74.5%, 75.0%, 75.5%, 76.0%, 76.5%, 77.0%, 77.5%, 78.0%, 78.5%, 79.0%, 79.5%, 80.0%, 80.5%, 81.0%, 81.5%, 82.0%, 82.5%, 83.0%, 83.5%, 84.0%, 84.5%, 85.0%, 85.5%, 86.0%, 86.5%, 87.0%, 87.5%, 88.0%, 88.5%, 89.0%, 89.5%, 90.0%, 90.5%, 91.0%, 91.5%, 92.0%, 92.5%, 93.0%, 93.5%, 94.0%, 94.5%, 95.0%, 95.5%, 96.0%, 96.5%, 97.0%, 97.5%, 98.0%, 98.5%, 99.0%, or 99.5%.

Examples of co-solvents include, but are not limited to, alcohols, silicones, polyglycols, glycols, and combinations thereof. In an embodiment, a co-solvent is diethylene glycol monoethyl ether (DGMEE). In an embodiment, a co-solvent is propylene glycol.

In an embodiment, a composition comprises DMSO in the range of about 0.01% to 99.99% and further comprises at least one penetrant in the range of 0.01% to about 99.99%. In an embodiment, a composition comprises DMSO and further comprises at least one penetrant in the range of about 0.1% to about 50%. In another embodiment, a composition comprises DMSO and further comprises at least one penetrant in the range between about 5% and about 50%. In another embodiment, a composition comprises DMSO and further comprises at least one penetrant in the range between about 10% and about 99%. In an embodiment, a composition comprises DMSO, at least one co-solvent, and at least one penetrant. In an embodiment, a co-solvent is also a penetrant.

In an embodiment, a composition comprises a gelling agent in weight percent in the range having a lower limit of 0.1% and an upper limit of 10.0%. The lower limit of the range of gelling agent in the composition can be 0.1%, 0.5%, 1.0%, 1.5%, 2.0%, 2.5%, 3.0%, 3.5%, 4.0%, 4.5%, 5.0%, 5.5%, 6.0%, 6.5%, 7.0%, 7.5%, 8.0%, 8.5%, 9.0%, 9.5%, or 9.9%. The upper limit of the range of gelling agent in the composition can be 0.5%, 1.0%, 1.5%, 2.0%, 2.5%, 3.0%, 3.5%, 4.0%, 4.5%, 5.0%, 5.5%, 6.0%, 6.5%, 7.0%, 7.5%, 8.0%, 8.5%, 9.0%, 9.5%, or 10.0%.

In a preferred embodiment, a composition of the invention comprises about 10% or less of a gelling agent, or comprises about 9% or less gelling agent, or comprises about 8% or less gelling agent or comprises about 7% or less gelling agent, or comprises about 6% or less gelling agent, or comprises about 5% or less gelling agent or comprises about 4% or less gelling agent or comprises about 3% or less gelling agent, or comprises about 2% or less gelling agent or comprises about 1% or less gelling agent. A preferred composition comprises from about 1% to about 5% gelling agent, from about 1.5% to about 4% gelling agent, from about 1.5% to about 3.5% gelling agent, from about 1.5% to about 3.0% gelling agent, from about 1.75% to about 2.5% gelling agent, or about 1% gelling agent, or about 2% gelling agent, or about 3% gelling agent.

In various embodiments, the compositions encompassed herein can comprise pharmaceutically acceptable excipients such as those listed in REMINGTON: THE SCIENCE AND PRACTICE OF PHARMACY 866-885 (Alfonso R. Gennaro ed. 19th ed. 1995; Ghosh, T. K.; et al. TRANSDERMAL AND TOPICAL DRUG DELIVERY SYSTEMS (1997), hereby incorporated herein by reference, including, but not limited to, protectives, adsorbents, demulcents, emollients, preservatives, antioxidants, moisturizers, buffering agents, solubilizing agents, skin-penetration agents, and surfactants.

In various embodiments, the compositions encompassed herein comprise pharmaceutically acceptable excipients such as those listed in the FDA Inactive Ingredients database-Updated Through Mar. 5, 2018, as found at: https://www.fda.gov/Drugs/InformationOnDrugs/ucm 113978.htm, which is hereby incorporated herein by reference, including, but not limited to, protectives, adsorbents, demulcents, emollients, preservatives, antioxidants, moisturizers, buffering agents, solubilizing agents, skin-penetration agents, and surfactants.

Protectives and adsorbents include, but are not limited to, dusting powders, zinc sterate, collodion, dimethicone, silicones, zinc carbonate, aloe vera gel and other aloe products, vitamin E oil, allatoin, glycerin, petrolatum, and zinc oxide.

Demulcents include, but are not limited to, benzoin, hydroxypropyl cellulose, hydroxypropyl methylcellulose, and polyvinyl alcohol.

Emollients include, but are not limited to, animal and vegetable fats and oils, myristyl alcohol, alum, and aluminum acetate.

Preservatives include, but are not limited to, chlorine dioxide, quaternary ammonium compounds, such as benzalkonium chloride, benzethonium chloride, cetrimide, dequalinium chloride, and cetylpyridinium chloride; mercurial agents, such as phenylmercuric nitrate, phenylmercuric acetate, and thimerosal; alcoholic agents, for example, chlorobutanol, phenylethyl alcohol, and benzyl alcohol; antibacterial esters, for example, esters of parahydroxybenzoic acid; and other anti-microbial agents such as chlorhexidine, chlorocresol, benzoic acid and polymyxin.

Suitable antioxidants include, but are not limited to, ascorbic acid and its esters, sodium bisulfite, butylated hydroxytoluene, butylated hydroxyanisole, tocopherols, and chelating agents like EDTA and citric acid.

Suitable moisturizers include, but are not limited to, glycerin, sorbitol, polyethylene glycols, urea, and propylene glycol.

Suitable buffering agents for use with the invention include, but are not limited to, acetate buffers, citrate buffers, phosphate buffers, lactic acid buffers, and borate buffers.

Suitable solubilizing agents include, but are not limited to, quaternary ammonium chlorides, cyclodextrins, benzyl benzoate, lecithin, and polysorbates, alcohol, octylphenylpolyethylene glycol, oleic acid, polyethylene glycol 400, propylene glycol, N-decylmethylsulfoxide, fatty acid esters (e.g., isopropyl myristate, methyl laurate, glycerol monooleate, and propylene glycol monooleate); and N-methylpyrrolidone.

Methods of Preparation and Use

In an embodiment, a method of treating a subject having a skin disease or condition selected from acne, dermatitis, rosacea, common warts, molluscum contagiosum, onychomycosis, and paronychia includes administration of a composition set forth, described, and/or encompassed herein to treat the skin condition or disease. The treatment of the skin disease or condition includes at least one of preventing or slowing the progression of the infection, preventing the spread of the infection, eradicating at least some of the infection, and eradicating the entire infection or lesions symptomatic of the skin disease or condition.

In an embodiment, a method of treating a subject having a skin disease complicated by microbial colonization and/or infection includes administration of a composition set forth, described, and/or encompassed herein to treat the skin disease, and the treatment of the skin disease includes at least one of preventing or slowing the progression of the infection, preventing the spread of the infection, eradicating at least some of the infection, and eradicating the entire infection.

In an embodiment, a therapeutic composition is administered on a schedule once a day. In an embodiment, a therapeutic composition is administered twice a day. In an embodiment, a therapeutic composition is administered three times a day. In an embodiment, a therapeutic composition is administered four times a day. In an embodiment, a therapeutic composition is administered five times a day, or more. In an embodiment, a therapeutic composition is administered less frequently than once a day. In an embodiment, a therapeutic composition is administered once every two days, once every three days, once every four days, once every five days, once every six days, or once every seven days. In an embodiment, a therapeutic composition is administered less frequently than once a week. In an embodiment, a therapeutic composition is administered once a month. In an embodiment, a therapeutic composition is administered twice a month.

In an embodiment, a therapeutic dosing regimen is continued for at least one day, at least two days, at least three days, at least four days, at least five days, at least six days, or at least seven days. In an embodiment, a therapeutic dosing regimen is continued for at least one week, at least two weeks, at least three weeks, at least four weeks, at least six weeks, at least eight weeks, at least 10 weeks, at least 12 weeks, at least 14 weeks, or at least 16 weeks. In an embodiment, a therapeutic dosing regimen is continued for at least one month, at least two months, at least three months, at least four months, at least five months, at least six months, at least nine months, or at least twelve months.

In an embodiment, a therapeutic dosing regimen includes administering a composition of the invention as needed (prn). In an embodiment, a therapeutic dosing regimen includes administering a composition of the invention in any of the above-described dosing regiments up to about 20 weeks or until the disease or condition is eliminated.

The invention is further described by the following examples. In an aspect, the following examples demonstrate effective and/or successful treatment of the identified conditions using compositions and methods encompassed by the present disclosure.

EXAMPLES

Example 1—Clinical Results of Treatment of MCV Infection with a Composition of DMSO, HEC and Water Molluscum contagiosum (MC) is a common, highly contagious viral infection that most frequently occurs in children. The disease typically persists for 6-18 months before spontaneous resolution. There is no standard therapy for infection or approved treatment. A clinical study was conducted to evaluate a specific embodiment of the subject invention composition. The composition was studied prospectively for efficacy in reducing the number of MCV lesions at several time points.

Subjects were allowed to participate in the study if they met all of the inclusion criteria and none of the exclusion criteria. Among the inclusion criteria were the following:

Males or females aged 2-18 years at screening;

MC diagnosed by a general physician, dermatologist or pediatrician who refers it and treatable by a topical agent;

Individuals with at least 1, but not exceeding 15 molluscum lesions selected in designated treatment area located anywhere on the body except for the following prohibited areas which include: eye area (including eyelids), lips, mouth cavity, nasal cavity, inner ear, palms of the hands, soles of the feet or the anogenital area.

Among the exclusion criteria were the following:

Mentally incompetent or unable or not willing to give written informed consent via parent or guardian or meet study requirements Significant atopic dermatitis surrounding the molluscum contagiosum lesions as judged by the investigator Individual lesions greater than 5 mm in diameter Pregnant, breastfeeding or unwilling to undergo an acceptable form of contraception for the duration of the study;

Have any uncontrolled current infection.

A specific embodiment of the subject composition comprising an aqueous gel solution of 44% DMSO, 2% HEC and 32% water and not containing any additional antiviral, antibacterial, antifungal, antiseptic or iodine-containing or iodophor containing agents was studied in a prospective clinical trial of pediatric subjects with a confirmed diagnosis of MCV infection.

Subjects were instructed to topically apply a small pea sized amount of gel to each lesion in the affected area twice daily. Written instructions were also provided. The total duration of the treatment was 60 days.

Presence of MC was documented, and the diagnosis confirmed by the general physician, dermatologist or pediatrician who refers it.

The primary outcome measure is complete resolution of baseline MC lesions at 60-day visit.

The investigator selected 15 or fewer lesions in the same general anatomical area for treatment. The investigator placed transparency paper over the body site that will receive treatment and demarcated the treatment area with a marker. The investigator then circled 15 (or less if total number is lower than 15) individual lesions designated for treatment within the demarcated area on the transparency paper.

The number of lesions circled was documented on the topography map in the space provided. At each subsequent follow up visit, the transparency paper marked at the baseline visit was placed over lesions in identical orientation and assessed for resolution. Lesions that have resolved were marked with an "X" through the corresponding circle and dated. The number of lesions remaining at each visit was documented on the topography map in the space provided.

Safety parameters were assessed by the investigator. Clinical cutaneous safety evaluations included reporting of scaling/peeling, dryness and erythema on a scale of 0-3 (0=absent, 1=mild. 2=moderate, 3=severe). Tolerability was assessed by subjects.

At the conclusion of the study, over 40% of the subjects achieved a clinical cure as defined by reaching the primary outcome measure. Of all 296 lesions present at the baseline visit, 203 were completely cleared by the final study visit.

Example 2—Clinical Study for Treatment of Common Warts with a Composition of DMSO, HEC and Water Verruca vulgaris is a common, contagious viral infection highly recalcitrant to available treatments. A clinical study will be conducted to evaluate a specific embodiment of the subject invention composition. The composition will be studied prospectively for efficacy in reducing the number of warts at several time points.

Subjects were allowed to participate in the study if they met all of the inclusion criteria and none of the exclusion criteria. Among the inclusion criteria were the following:

Males or females aged 18-99 years at screening;

Verruca vulgaris diagnosed by a general physician, dermatologist or pediatrician who refers it and treatable by a topical agent;

Individuals with at least 1, but not exceeding 15 warts selected in designated treatment area located anywhere on the body except for the following prohibited areas which include: eye area (including eyelids), lips, mouth cavity, nasal cavity, inner ear, palms of the hands, soles of the feet or the anogenital area.

Among the exclusion criteria were the following:

Mentally incompetent or unable or not willing to give written informed consent via parent or guardian or meet study requirements Significant atopic dermatitis surrounding the wart as judged by the investigator Individual lesions greater than 5 mm in diameter Pregnant, breastfeeding or unwilling to undergo an acceptable form of contraception for the duration of the study;

Have any uncontrolled current infection.

A specific embodiment of the subject composition comprising an aqueous gel solution of 44% DMSO, 2% HEC and water and not containing any additional antiviral, antibacterial, antifungal, antiseptic or iodine-containing or iodophor containing agents will be studied in a prospective clinical trial of subjects with a confirmed diagnosis of Verruca vulgaris wart or lesion.

Subjects will be instructed to topically apply a small pea sized amount of gel to each wart in the affected area twice daily. Written instructions will also be provided. The total duration of the treatment is 60 days.

Presence of warts will be documented, and the diagnosis confirmed by the general physician, dermatologist or pediatrician who refers it.

The primary outcome measure is complete resolution of baseline warts at 60-day visit.

The investigator will select 15 or fewer lesions in the same general anatomical area for treatment. The investigator places transparency paper over the body site that will receive treatment and demarcate the treatment area with a marker. The investigator then circles 15 (or less if total number is lower than 15) individual warts designated for treatment within the demarcated area on the transparency paper.

The number of warts circled will be documented on the topography map in the space provided. At each subsequent follow up visit, the transparency paper marked at the baseline visit will be placed over the warts in identical orientation and assessed for resolution. Warts that have resolved are marked with an "X" through the corresponding circle and dated. The number of lesions remaining at each visit will be documented on the topography map in the space provided.

Safety parameters are assessed by the investigator. Clinical cutaneous safety evaluations include reporting of scaling/peeling, dryness and erythema on a scale of 0-3 (0=absent, 1=mild. 2=moderate, 3=severe). Tolerability is assessed by subjects.

At the conclusion of the study, over 40% of the subjects are expected to achieve a clinical cure as defined by reaching the primary outcome measure.

Example 3—Clinical Study for Treatment of Onychomycosis with a Composition of DMSO, HEC and Water Onychomycosis is a fungal infection of the fingernail or toenail (nail), highly recalcitrant to available treatments. A clinical study will be conducted to evaluate a specific embodiment of the subject invention composition. The composition will be studied prospectively for efficacy in reducing the severity of the nail infection at several time points.

Subjects were allowed to participate in the study if they met all of the inclusion criteria and none of the exclusion criteria. Among the inclusion criteria were the following:

Males or females aged 18-99 years at screening;

Onychomycosis diagnosed by a general physician, dermatologist or pediatrician who refers it and treatable by a topical agent;

Individuals with at least 1, but not exceeding 15 infected nails.

Among the exclusion criteria were the following:

Mentally incompetent or unable or not willing to give written informed consent via parent or guardian or meet study requirements Pregnant, breastfeeding or unwilling to undergo an acceptable form of contraception for the duration of the study;

Have any uncontrolled current infection.

A specific embodiment of the subject composition comprising an aqueous gel solution of 44% DMSO, 2% HEC and water and not containing any additional antiviral, antibacterial, antifungal, antiseptic or iodine-containing or iodophor containing agents will be studied in a prospective clinical trial of subjects with a confirmed diagnosis of onychomycosis.

Subjects will be instructed to topically apply a small pea sized amount of gel to each infected nail twice daily. Written instructions will also be provided. The total duration of the treatment is 60 days.

Presence of onychomycosis will be documented, and the diagnosis confirmed by the general physician, dermatologist or pediatrician who refers it.

The primary outcome measure is complete resolution of baseline onychomycosis at 60-day visit.

Safety parameters are assessed by the investigator. Clinical cutaneous safety evaluations include reporting of scaling/peeling, dryness and erythema on a scale of 0-3 (0=absent, 1=mild. 2=moderate, 3=severe). Tolerability is assessed by subjects.

At the conclusion of the study, over 40% of the subjects are expected to achieve a clinical cure as defined by reaching the primary outcome measure.

Example 4—Clinical Study for Treatment of Paronychia with a Composition of DMSO, HEC and Water Paronychia is a common infection of the tissue surrounding the fingernail or toenail (nail), highly recalcitrant to available treatments. A clinical study will be conducted to evaluate a specific embodiment of the subject invention composition. The composition will be studied prospectively for efficacy in reducing the severity of the paronychia infection at several time points.

Subjects were allowed to participate in the study if they met all of the inclusion criteria and none of the exclusion criteria. Among the inclusion criteria were the following:

Males or females aged 18-99 years at screening;

Paronychia diagnosed by a general physician, dermatologist or pediatrician who refers it and treatable by a topical agent;

Individuals with at least 1, but not exceeding 15 infected nails.

Among the exclusion criteria were the following:

Mentally incompetent or unable or not willing to give written informed consent via parent or guardian or meet study requirements Pregnant, breastfeeding or unwilling to undergo an acceptable form of contraception for the duration of the study;

Have any uncontrolled current infection.

A specific embodiment of the subject composition comprising an aqueous gel solution of 44% DMSO, 2% HEC and water and not containing any additional antiviral, antibacterial, antifungal, antiseptic or iodine-containing or iodophor containing agents will be studied in a prospective clinical trial of subjects with a confirmed diagnosis of paronychia.

Subjects will be instructed to topically apply a small pea sized amount of gel to each infected area of the nail twice daily. Written instructions will also be provided. The total duration of the treatment is 60 days.

Presence of paronychia will be documented, and the diagnosis confirmed by the general physician, dermatologist or pediatrician who refers it.

The primary outcome measure is complete resolution of baseline paronychia at 60-day visit.

Safety parameters are assessed by the investigator. Clinical cutaneous safety evaluations include reporting of scaling/peeling, dryness and erythema on a scale of 0-3 (0=absent, 1=mild. 2=moderate, 3=severe). Tolerability is assessed by subjects.

At the conclusion of the study, over 40% of the subjects are expected to achieve a clinical cure as defined by reaching the primary outcome measure.

It should be recognized that variations based on the inventive features are within the skill of the ordinary artisan, and that the scope of the invention should not be limited by the examples. To properly determine the scope of the invention, an interested party should consider the claims herein, and any equivalent thereof. In addition, all citations herein are incorporated by reference, and unless otherwise expressly stated, all percentages are by weight.

It should be recognized that variations based on the inventive features are within the skill of the ordinary artisan, and that the scope of the invention should not be limited by the examples. To properly determine the scope of the invention, an interested party should consider the claims herein, and any equivalent thereof. In addition, all citations herein are incorporated by reference, and unless otherwise expressly stated, all percentages are by weight.

It will be appreciated by those skilled in the art that changes could be made to the exemplary embodiments shown and described above without departing from the broad inventive concept thereof. It is understood, therefore, that the disclosure herein is not limited to the exemplary embodiments shown and described, but it is intended to cover modifications within the spirit and scope of the present invention as defined by the claims. For example, specific features of the exemplary embodiments may or may not be part of the claimed invention and features of the disclosed embodiments may be combined. Unless specifically set forth herein, the terms "a", "an" and "the" are not limited to one element but instead should be read as meaning "at least one".

It is to be understood that at least some of the descriptions of the invention have been simplified to focus on elements that are relevant for a clear understanding of the invention, while eliminating, for purposes of clarity, other elements that those of ordinary skill in the art will appreciate may also comprise a portion of the invention. However, because such elements are well known in the art, and because they do not necessarily facilitate a better understanding of the invention, a description of such elements is not provided herein.

Further, to the extent that the method does not rely on the particular order of steps set forth herein, the particular order of the steps should not be construed as limitation on the claims. The claims directed to the method of the present invention should not be limited to the performance of their steps in the order written, and one skilled in the art can readily appreciate that the steps may be varied and still remain within the spirit and scope of the present invention.

The invention claimed is:

1. A method for treating molluscum contagiosum comprising the steps of:
    a) providing a composition comprising a single effective agent,
       1%-3% gelling agent, and water or isotonic buffer as a solvent wherein the single effective agent is DMSO at a concentration of 40-45% by weight of the composition;
    b) topically administering an effective amount of said composition to a molluscum contagiosum lesion at least once per day up to four times per day; and
    c) optionally, repeating the topical administration of step b) for a period of two days up to about eight weeks until the molluscum contagiosum lesion is clinically cured.

2. A method for providing a clinical cure rate of 40% against a molluscum contagiosum virus lesion, wherein the clinical cure is resolution and elimination of the lesion within eight weeks following topical administration to the lesion at least once per day up to four times per day of a composition comprising
    a single effective agent,
    1%-3% gelling agent, and
    water or isotonic buffer as a diluent or solvent,
wherein the single effective agent is DMSO at a concentration of 40-45% by weight of the composition.

3. The method of claim 1, wherein the DMSO concentration is 44% by weight of the composition.

4. The method of claim 2, wherein the DMSO concentration is 44% by weight of the composition.

5. The method of claim 1 wherein the composition comprises 2% gelling agent.

6. The method of claim 1 wherein the gelling agent is a cellulosic polymer.

7. The method of claim 1 wherein the gelling agent is hydroxyethyl cellulose.

8. The method of claim 1 wherein the composition is free of an iodophor.

9. The method of claim 2 wherein the composition comprises 2% gelling agent.

10. The method of claim 2 wherein the gelling agent is a cellulosic polymer.

11. The method of claim 2 wherein the gelling agent is hydroxyethyl cellulose.

12. The method of claim 2 wherein the composition is free of an iodophor.

13. A method for treating molluscum contagiosum comprising the steps of:
    a) providing a composition consisting essentially of a single effective agent,
       2% gelling agent, and water or isotonic buffer as a solvent;
       wherein the single effective agent is DMSO at a concentration of 44% by weight of the composition; and
       wherein the gelling agent is hydroxyethyl cellulose;
    b) topically administering an effective amount of the composition to a molluscum contagiosum lesion at least once per day up to four times per day; and
    c) repeating the topical administration of step b) for a period of two days up to about eight weeks until the molluscum contagiosum lesion is clinically cured.

14. A method for treating molluscum contagiosum comprising the steps of:
    a) providing a composition consisting of a single effective agent,
       2% gelling agent, and water or isotonic buffer as a solvent;
       wherein the single effective agent is DMSO at a concentration of 44% by weight of the composition;
       wherein the gelling agent is hydroxyethyl cellulose; and
       wherein the composition is free of an iodophor;
    b) topically administering an effective amount of the composition to a molluscum contagiosum lesion at least once per day up to four times per day; and
    c) repeating the topical administration of step b) for a period of two days up to about eight weeks until the molluscum contagiosum lesion is clinically cured.

* * * * *